(12) United States Patent
Van Gansberghe et al.

(10) Patent No.: US 6,800,767 B2
(45) Date of Patent: Oct. 5, 2004

(54) METHOD FOR PURIFYING CYCLIC ESTERS

(75) Inventors: Frédéric Van Gansberghe, Brussels (BE); Philippe Coszach, Brussels (BE); Patricia Di Salvatore, Brussels (BE); Jean-Christophe Bogaert, Brussels (BE)

(73) Assignee: Brussels Biotech, Brussels (BE)

( * ) Notice: Subject to any disclaimer, the term of this patent is extended or adjusted under 35 U.S.C. 154(b) by 0 days.

(21) Appl. No.: 10/239,584

(22) PCT Filed: Mar. 22, 2001

(86) PCT No.: PCT/BE01/00047
§ 371 (c)(1), (2), (4) Date: Jan. 13, 2003

(87) PCT Pub. No.: WO01/70721
PCT Pub. Date: Sep. 27, 2001

(65) Prior Publication Data
US 2004/0014991 A1 Jan. 22, 2004

(30) Foreign Application Priority Data
Mar. 23, 2000 (EP) ............................................. 00870052

(51) Int. Cl.$^7$ ............................................. C07D 407/00
(52) U.S. Cl. ....................................................... 549/274
(58) Field of Search ........................................ 549/274

(56) References Cited

U.S. PATENT DOCUMENTS 6,489,508 B1 * 12/2002 Van Gansbeghe et al. .. 562/589

FOREIGN PATENT DOCUMENTS

EP 657447 A1 * 6/1995

* cited by examiner

*Primary Examiner*—Amelia A. Owens

(57) ABSTRACT

The invention concerns a method for purifying the dimeric cyclic esters of lactic (or glycolic) acid starting from a raw lactide (or glycolide) comprising impurities, the method consisting in: extractive and controlled crystallization of the raw lactide, in aqueous medium, controlling the geometry of the formed crystals and carrying out a separation of phases into lactide and impurities; separation of the resulting suspension of crystals, into a phase poor in lactide and loaded with impurities, and a wet cake rich in lactide crystals; drying the resulting wet cake; and recrystallization in melted medium of the resulting dried impure lactide and recuperating the purified lactide.

31 Claims, No Drawings

METHOD FOR PURIFYING CYCLIC ESTERS

FIELD OF THE INVENTION

The present invention relates to a process for purifying dimeric cyclic esters (especially lactides or glycolides) of general formula:

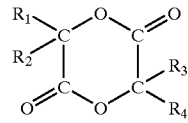

where $R_1$, $R_2$, $R_3$, and $R_4$ may alternatively be a hydrogen, an aromatic group or a substituted or unsubstituted aliphatic group having from 1 to 10 carbon atoms. These esters can be converted into polymers which are particularly useful for preparing biodegradable and bioabsorbable plastics in medicine. The polymers of lactide (where $R_1=R_3=H$ and $R_2=R_4=CH_3$) are degradable by aqueous hydrolysis under the majority of environmental conditions, giving lactic acid or oligomers.

The two optically active forms of lactic acid (L-LA) and (D-LA) may give a lactide (LD or cyclic dimer) in 3 diastereoisomeric forms: with 2 molecules of D-lactic acid (D,D-lactide or D-LD), with 2 molecules of L-lactic acid (L,L-lactide or L-LD), or with one molecule of each (meso-lactide or meso-LD). Also encountered is the racemic mixture ((D,L)-lactide) characterized by a melting point (Tf=126° C.) greater than that of L-LD or D-LD (Tf=97° C.).

Presently, the two major methods of producing lactide are distinguished essentially by the average degree of polymerization (DP) of the oligomers from the condensation step.

The first consists in extracting the water from a solution of lactic acid to obtain oligomers where $8 \leq DP \leq 25$. These oligomers are subsequently depolymerized (back-biting reaction) with a Lewis acid catalyst, either under reduced pressure at a higher or lower temperature or under a stream of nitrogen. This process is realized under severe conditions which prove expensive and affect the optical purity of the lactide (high percentage of racemization).

The second method utilizes an oligomer where $1.5 \leq DP \leq 2.5$ produced in vapor phase at high temperature or in liquid phase in the presence of a cosolvent which forms an azeotrope with water. The principal drawbacks are the presence of a solvent, often an aromatic solvent, with a high boiling point; a reaction temperature >180° C.; a lack of selectivity; and a not inconsiderable quantity of protic impurities.

In general, the crude lactide obtained by various synthesis routes includes a number of protic impurities (carboxylic acids, hydroxyl compounds, water, etc.) which must be extracted in order to provide a sufficient purity for the crude product to be integrated to the process of polymerization by ring opening.

PRIOR ART

Percentages will always be expressed by weight in the remainder of this text.

The skilled worker is aware of CA 2 115 472, which proposes a process for purification by dynamic crystallization in the melt state, with recovery of meso-LD in an enriched form. However, the process is applicable only to crude lactides having L-LD/D-LD ratios of at least 80/20 or at least 20/80. Where the composition of the crude product is found to correspond to a composition beyond the eutectic, there is then an enrichment which racemic mixture L-LD+D-LD, with rejection of the L-LD together with the impurities such as water, lactic acid and the oligomers. On the other hand, it is necessary to start from a crude lactide which is already rich in lactides (>90% L-LD+meso-LD).

U.S. Pat. No. 5,502,215 relates to a process for purifying crude lactide which comprises crystallizing L-LD and/or D-LD in an aqueous medium followed by centrifugal separation, gas-phase drying, and recrystallization from an organic solvent with centrifugal separation and gas-phase drying and, where appropriate, rinsing with this organic solvent. The emphasis is on the removal of the meso-LD by hydrolysis and not on the extraction of protic impurities by water. On the other hand, the aim is not to produce lactide crystals of a particular type.

The two purification methods described above, which make it possible to treat a variety of crude lactides and to obtain purities of the order of 99%, which allows polymerization to polylactide (PLA) under tolerable conditions. However, these methods involve either large yield losses due to the opening, the chemical racemization and/or the thermal racemization of the lactide ring or high investment costs and exploitation costs tied to the needs for storage and treatment which are associated with a solvent purification procedure.

The present invention overcomes these drawbacks and makes it possible to produce a lactide which is sufficiently pure for polymerization under good economic conditions.

BRIEF DESCRIPTIONS OF THE INVENTION

The present invention provides a process for purifying cyclic esters, especially the cyclic dimer of lactic acid (lactide), starting from a "crude lactide", namely a mixture of lactic acid and/or lactic ester and their respective oligomers ($L_nA$ with n<5), water and/or alcohol and also various diastereoisomeric forms of lactide.

This crude product may be obtained either starting from lactic acid, and/or its salts and/or its esters originating from any synthesis known to the skilled worker, a nonexhaustive description of which has been set out above, or starting from residues from purification processes such as distillation or crystallization in a melt medium.

We will always refer below to the synthesis of lactide starting from lactic acid, although it may also be applied to the esters of lactic acid. By lactide is meant one of the two diastereoisomeric forms (L-LD or D-LD) and not meso-LD.

The purification process described in this invention is original since, starting from a crude lactide (even one poor in lactide), it provides a very high quality of lactide with a high mass yield and a minimum energy consumption. A lactide of very high quality (chemical or optical quality) may serve as a monomer for the synthesis of PLA by ring opening.

The quantitative and selective process is assured by the joint employment: (a) of controlled, extractive crystallization of the lactide in an aqueous medium, in order to promote the formation of large crystals and the transfer of the protic impurities to the liquid phase, (b) of centrifugal or other separation (with or without washing) of the lactide and of the aqueous phase, (c) of solid-phase or liquid-phase drying of the moist cake obtained, and (d) of one or more recrystallizations in a melt medium.

This sequence allows easy and quantitative recycling of the aqueous-phase impurities to the lactic acid production procedure. Optimizing the temperature and residence time conditions makes it possible, in contrast to the conventional processes, to avoid chemical and thermal deterioration of the lactide in the course of its purification. The industrial criteria of quality and of yield are attained much more readily.

The energy outlay is minimal owing to the simplicity of the technologies, to the low operating temperatures, and to the judicious juxtaposition of the steps. Recrystallization in a melt medium is known to the skilled worker, since it makes it possible to obtain a lactide of excellent quality and a selectivity which is necessary for the synthesis of PLA. However, starting from a lactide-poor crude lactide, this technology does not make it possible both to guarantee an adequate yield of lactide and to withstand an economic comparison vis-à-vis other technologies (distillation, recrystallization from solvent, etc.). On the other hand, the succession of steps (a) to (d) and the methodology recommended by the present invention compensate for handicap.

DETAILED DESCRIPTION OF THE INVENTION

Preferentially, the starting mixture will have a composition in terms of one of the lactides of between 30 and 90% and preferably between 40 and 85%, in terms of water (when working with an ester, the water will be replaced by an alcohol) of between 0 and 2% and preferably between 0 and 1%, in terms of lactic acid and its oligomers ($L_n$A with n<5) of between 0 and 50%, the remainder (the meso-LD and the other diastereoisomer of lactide) of between 0 and 30%.

This mixture or crude product originates from the extraction, at a specific point in the condensation step, of the vapors obtained by the synthesis of the cyclic dimer of lactic acid. It is also possible to recover the fractions obtained from purification processes (distillation or crystallization in a melt medium) whose lactide content is too low for them to be purified but which is sufficient for recycling as lactide and not as a source of lactic acid (hydrolysis of the lactide).

This process essentially comprises the following steps:
(a) A Controlled, Extractive Crystallization This consists in a quantitative, selective, and controlled crystallization of the lactide in an aqueous medium with concentration of the protic impurities in the liquid phase, by addition of water.

Coupled with the step of centrifugal separation (b) and that of drying (c), it constitutes a prepurification which gives a mixture whose selectivity (LD content) is sufficient for a final, effective and profitable purification by recrystallization in a melt medium (d). The high selectivity will give an LD content of more than 90% and preferably more than 95%, without taking into account the added water.

Relative to existing processes of extraction with water, here the major part of the meso-LD is not removed by hydrolysis of the ring, but the geometry of the crystals formed is controlled, a phase segregation is brought about between the lactide (solid phase) and the impurities (liquid phase), and the extraction of the soluble protic impurities is promoted. A reduction in the meso-LD content cannot be completely avoided. The final step of the process will allow effective and sterospecific separation of the lactide and of the meso-LD; it is therefore necessary to avoid hydrolyzing the latter by ring opening. For certain applications, the recovery of the meso-LD and its use for PLA constitute a major asset.

This process allows the impurities to be recycled to the production of lactide from lactic acid, allows the geometry of the crystals to be controlled, allows effective aqueous extraction of the protic impurities, and permits reaction conditions which are very gentle in order to prevent yield losses by chemical or thermal opening of the lactide.

The present invention recommends initial and final temperatures of the mixture [crude lactide+water used for the extraction] not exceeding 100° C. and 50° C. respectively, preferably less than 90° C. and 35° C., and more preferably still less than 80° C. and 25° C., and residence times of between 1 and 90 min, preferably between 1 and 60 min, in order to initiate and complete the extraction, so as to reduce racemization and the energy outlay and to enhance the productivity of the process.

However, the asset of an inappropriate quantity of water creates problems of transfer, of extraction efficiency or of crystallization control. This is because too large an amount of water allows hydrolysis of the meso-LD but also hydrolysis of the lactide by ring opening (which considerably effects the yield). In the known extraction processes, this degradation is slowed by a very rapid decrease in the temperature of the mixture, which causes very significant nucleation within the mixture, and a solidification. This is of no detriment to the known extraction processes which are aimed at selective hydrolysis of the meso-LD present in crystalline form and not at aqueous extraction of the protic impurities (the purity of the starting product already being relatively high). In contrast, as far as the invention is concerned, nucleation and crystal growth must be controlled in order to prevent solidification, which reduces the efficiency of the extraction: the temperature drop causes a rise in the viscosity of the impurities (such as the lactic acid or the lactic acid oligomers) which are much more difficult to remove from the surface of the crystals, and also causes the formation of a block which is difficult to solvate with water.

Moreover, the solidification prevents the control of the geometry of the crystals, which are unable to develop a lamellar structure. These crystals in accordance with the invention, with neither inclusions or occlusions, are of greater purity, stability and manipulability.

In order not to promote hydrolysis of the meso-LD, in this invention the concentration of water added to the starting mixture will be less, between 0 and 40%, preferably between 0 and 30%, and more preferably between 0 and 20%. The degradation of the lactide is then much slower and allows better control of the temperature and of the crystallization, since there is a specific crystallization temperature corresponding to each lactide composition of the crude lactide. In a first phase, the mixture will be brought to 10° C., preferably to 5° C. and more preferably to 2° C. below this temperature and will be held there for between 1 and 45 min, preferably between 1 and 30 min, and more preferably still between 1 and 15 min. One approach of the invention consists in setting the temperature of the added water such that, after mixing, its temperature corresponds to the desired holding temperature. A second approach of the invention consists in initiating the crystallization of the crystals of pure lactide (progressive seeding).

During the following phase of the first step, the temperature of the mixture is slowly reduced in order to provoke progressive growth of the crystals and to enhance the yield. This control of the crystallization procedure gradually pushes the impurities into the liquid phase, and crystals having a lamellar structure, without inclusion, are formed. The geometry of crystals which are obtained considerably increases the efficiency of the two steps of separation (b) and of drying (c). On the other hand, with a water content close to 1%, the chemical stability of the lactide crystals is increased over those obtained by solidification of the mixture.

In the present invention, the reactor will provide effective agitation in order to distribute the heat over the entirety of the mixture, will avoid solidification, and will allow easy evacuation of the mixture from the reactor. Its large thermostating capacity will promote progressive crystallization (yield) and controlled crystallization (crystal growth) of the lactide. Any batch or continuous reactor which conforms with these requirements is appropriate, such as a batch reactor coupled with an external heat exchanger. Moreover, the skilled worker is also able to envisage sonocrystallization or crystal seeding to promote the crystallization of the lactide.

In contrast to the known processes of extraction with water, this new method of working promotes the appearance of one particular form of lactide.

GC analysis of the products obtained from this controlled, extractive crystallization made it possible to observe the appearance of an additional, unknown compound.

As a function of temperature, water concentration and contact time, the amount of this compound changed inversely to that of the lactide.

GC-MS, NMR ($^{13}$C, $^1$H) and IR analyses show that this compound was a molecule of lactide "complexed" by a molecule of water. This complex presupposes a relatively strong polar interaction but not a covalent chemical bond, since the analysis of the two molecules (the lactide and the complex) gave two totally identical mass spectra, with no additional peak at m/z 162, which tends to prove the existence of a complex and not of a chemical bond. The NMR and IR spectra show a modification which definitely corresponds to the presence of water.

This complex is not generated in the case of sudden cooling. Only the knowledge of the existence and nature of this complex makes it possible to correctly and effectively steer the steps of drying and of crystallization in a melt medium which are associated with this process.

(b) A Centrifugal Separation

Starting from a suspension obtained in (a) whose water content is between 1 and 40% by weight, preferably between 1 and 25% and more preferably still between 1 and 20%, the lactide (complex included) content is between 35 and 90%, preferably between 40 and 90%, and more preferably still between 45 and 90%, the amount of lactic acid and its oligomers ($L_nA$ with n<5) is between 0 and 10% and preferably between 0 and 5%, the remainder being meso-LD and the other diastereoisomer of the lactide, this step consists in centrifugal separation or other separation of the lactide, which is essentially present in the solid phase (cake), and the aqueous filtrates which are loaded with protic impurities.

The filtrates will easily be able to be recycled to the production of lactides starting from lactic acid, in order to increase the overall PLA synthesis yield.

Centrifugal separation is desirable: it is very rapid owing to the favorable geometry of the crystals generated in step (a). Moreover, the dryness of the cake makes it easy to handle the product. Furthermore, the chemical stability of the crystals prevents yield losses by ring opening.

One favored approach recommends a suction time sufficient to attain residual free water contents of between 0 and 3%, preferably between 0 and 1%, and more preferably between 0 and 0.5%.

In order to facilitate or suppress the following drying step, the filter cake is washed. Washing makes it possible to reduce the contact times to a minimum, and increases the yield. Any process will be suitable within the context of this invention.

The choice of the washing solvent makes it possible to eliminate in a simple way the impurities deposited in film form on the surface of the crystals, to reduce the residual water content of the cake, and to increase the chemical stability of the crystals. The solvent should be miscible with water (reduction in the residual water), should form a lower azeotrope with water (easier distillation of traces of water), should have a relatively low boiling point (economy), should be chemically inert with respect to the lactide (to prevent the opening of the ring), should be readily soluble with respect to the lactide (to avoid yield losses), should have a greater interaction with water than the lactide (to remove the water bound to the lactide). The difficult choice of the solvent will therefore result in a compromise between extraction efficiency, yield, and profitability of the process.

The solvents which can be used are ketones, ethers, aromatic or aliphatic hydrocarbons, silicone-based solvents, and halogenated solvents (acetone, 2-butanone, 2-pentanone, 2-hexanone, 2-heptanone, 2-octanone, anisole, ethyl ether, isopropyl ether, butyl ether, methyl phenyl ether, methyl isobutyl ketone, benzene, cumene, cymene, p-xylene, o-xylene, m-xylene, toluene, cyclohexane, hexane, heptane, octane, nonane, 1-pentene, 4-methylanisole, 1,2-dimethoxybenzene, 1,3-dimethoxybenzene, 1,4-dimethoxybenzene, mesitylene, chlorobenzene, 1,2-dichlorobenzene, 1,3-dichlorobenzene, 1,4-dichlorobenzene, 2-chlorotoluene, 3-chlorotoluene, 4-chlorotoluene, ethanol, isopropanol).

(c) Drying

Starting from a wet cake obtained in (b) with a water content of between 0 and 5%, preferably between 0 and 2%, and more preferably still between 0 and 1%, with a lactide content (complex included) between 75 and 98%, preferably between 85 and 98%, and more preferably still between 90 and 98%, the amount of lactic acid and its oligomers ($L_nA$ with n<5) being between 0 and 5%, preferably between 0 and 3%, and more preferably still between 0 and 1%, the remainder being meso-LD and the other diastereoisomer of the lactide, this step consists in evaporating the residual amounts of water. This step may also make it possible to extract all or some of the solvent introduced in the course of washing.

Moreover, the complex generated by this process will have to be handled meticulously: because its formation is reversible, the complex could release its water under certain conditions.

The wet cake obtained from step (b) will therefore have to be treated with account taken of the fact that it comprises free residual water and bound water (in complex form).

The low water (free+bound) content of the wet lactide, which is indispensable for ensuring the temporary chemical stability of the lactide, does not, however, allow final purification by recrystallization in a melt medium: this water content reduces the yield by ring opening during remelting procedures. One favored approach makes it possible to obtain a free residual water content of between 0 and 800 ppm, preferably between 0 and 600 ppm, more preferably between 0 and 400 ppm. Likewise, the complex content will have to be between 0 and 3%, preferably between 0 and 0.5%, and more preferably between 0 and 0.05%.

In the present context, two drying techniques may be considered for treating these amounts of water.

The first consists in treating the product obtained from step (b) in its initial form (solid). A dryer which offers a large volatilization capacity for the purpose of removing the water or the residual solvent will carry out drying under gentle and controlled conditions in order to prevent any thermal deterioration of the product. The drying operation is more delicate on account of the fact that the wet cake, in contrast to the other processes of extraction with water, contains meso-LD with a melting point between 45 and 50° C. it is appropriate to carry out drying at at least 50° C., under vacuum or under a flow of gas. Moreover, the complex, which is susceptible to releasing its water, also gives an incitement to work at a low temperature in order to prevent degradation of the lactide. Any drying process and any technology known to the skilled worker which promote the evaporation and extraction of the water or of a solvent from a wet solid will be envisaged within this invention: mixer-dryers operating under vacuum or under dry gas streams, the principle of zeodration, plate dryers, etc.

The second technique recommends liquefying the wet cake from step (b) and entraining the water (free+bound) by purging or sparging of a dry gas stream. As in the first technique, in order to ensure the chemical stability of the lactide, the drying temperature will be close to the minimum required to maintain the wet lactide in liquid form. Any drying process and technology which is known to the skilled worker which promotes the extraction of the water or of a solvent from a wet liquid will be envisaged within this context: a gas scrubbing column (stripping), a thin-film dryer, molecular sieves, etc.

On the other hand, if, during the washing of the cake with solvent, the residual water content following extraction is compatible with the melt-medium recrystallization described, and if the residual amount of solvent remains compatible from the chemical (no opening of the lactide by the solvent) and technical standpoint to the final step (no reduction in the solvent content during the process), this drying step can be avoided.

For the washing of the cake, the solvent will ideally form an azeotrope with water: it will be easy and profitable to extract the final traces of water and solvent so as to allow profitable exploitation of the final purification step.

(d) Recrystallization in a Melt Medium

The dry impure lactide obtained in (c), whose composition is similar to that of the product obtained from step (b) except for the lower free-water and bound-water content, will undergo a final purification by recrystallization in a melt medium (one or more stages) to give a lactide whose chemical and stereospecific purity is sufficient for the synthesis of PLA by ring opening. Sufficient purity implies an amount of one lactide of between 99.0 and 99.9% and more preferably between 99.5 and 99.9%, a meso-LD content of between 0 and 0.5% and preferably between 0 and 0.2%, a water content of between 0 and 100 ppm and preferably between 0 and 50 ppm, and an acidity of between 0 and 10 meq/kg and preferably between 0 and 1 meq/kg.

The dry impure lactide obtained in (c) is melted and undergoes controlled cooling in order to initiate crystallization. The impurities will be concentrated in the liquid phase. Following the crystallization, the liquid phase is removed by gravity, leaving crystals coated with a film of impurities. To eliminate the film, a partial remelting procedure is carried out. The liquid thus obtained entrains the film and is evacuated by gravity. The operation is repeated until the required purity is reached. This succession of steps may be static or dynamic.

Once the desired purity has been obtained, the contents of the crystallizer are melted and recovered.

This final purification step is exploitable quantitatively, economically, and energetically only by prior treatment of the crude lactide in accordance with the 3 steps above. The product arriving at the melt-medium recrystallization will be of a purity of more than 90% and more preferably of more than 95% for viable exploitation of the process. An inadequate purity considerably increases the number of operations and hence the investment costs.

A low free water content (<800 ppm and preferably <400 ppm) makes it possible to prevent rapid chemical deterioration of the lactide and a fall in productivity and yield. The water is concentrated in the liquid phase from the first step and gives rise to premature opening of the lactide owing to the heating cycles which are an inherent part of the technology. Since the process is based on the recycling of different fractions, the resultant loss then directly affects the final yield. The amount of complex in the product arriving at the melt-medium crystallization must be reduced sharply: the conditions of this step might cause release of the water originating from the complex.

The appropriate choice of the melt-medium recrystallization parameters makes it possible to recover the meso-LD by virtue of the low losses in step (a). This process serves for the synthesis of PLA with controlled degradation kinetics.

During the last step of the invention, the viscosity of the impurities in the product to be purified greatly influences the mass transfer coefficient during the crystallization and hence directly influences the shape of the crystals, the rate of crystallization, and the yield. The addition, to the starting product in step (d), of a solvent makes it possible to reduce the viscosity. This solvent may be mixed with the dry product from step (c) during a purification without solvent or may be the residue of solvent introduced during step (b) of the process. This amount may vary depending on whether a drying step (c) has been carried out or not.

This solvent must be present in concentrations which make it possible to maintain the industrial exploitation of our process, namely concentrations of between 0 and 30%, preferably between 0 and 20%, and more preferably between 0 and 10%. The addition of too great a quantity would be tantamount to a recrystallization from solution, which would require crystallizers of higher capacity, thereby canceling out the benefit of using a solvent. Said solvent must be inert with respect to the lactide and must be easily recycled into the overall PLA production process: mention may be made, for example, of the esters of lactic acid or a solvent from step (b).

Other details and particular features of the invention, given below by way of example without being limited to it, describe possible embodiments.

EXAMPLES

Example 1

A sample (feed) of crude lactide (0.696 kg) containing 83% of L-LD, 8% of meso-LD, and 1.6% of hydrated L-LD complex (complex) with a residual acidity of 570 meq/kg is introduced into a crystallizer consisting of a vertical stainless-steel tube with a length of 1 m and a diameter of 30 mm. The jacket of the tube is supplied with heat transfer fluid by a thermostated heating unit for controlling the phases of crystallization, of sweating or of remelting. This crude product is melted at 105° C.

Next, crystallization is initiated on the wall by a gradual reduction in the temperature of the heat transfer fluid present in the jacket. In order to prevent occlusions and inclusions within the pure crystals, this temperature reduction will be from 2 to 5° C./h. A portion of the crude product is crystallized on the walls, while the central part contains the liquid phase (drain) containing the majority of the impurities.

When the heat transfer fluid has been brought to 60° C., the liquid phase is extracted by gravity.

The crystals are still covered with a film of impurities, which the sweating step is required to eliminate: the surface of the tube will be very gradually heated (from 60 to 98° C.) so as to cause the surface of the crystals of least purity to melt, since their melting point is lower than that of the pure product. Depending on the nature of the crude product, the sweating fraction harvested by gravity represents from 5 to 25% of the initial charge.

Finally, the crystallizer is brought (at 4° C./min) to the melting of the product (97–102° C.) in order to liquefy all of the substance harvested by gravity (melt).

An end product which is required to meet the specifications of a lactide for synthesis of PLA will undergo a second and even a third stage of purification by the same procedure.

Table I shows the enrichment of the intermediate fractions with impurities and also the increase in the mass yield of the harvested fractions, as a function of the stages.

TABLE I

|  | STAGE 1 | | | STAGE 2 | | | STAGE 3 | | |
| --- | --- | --- | --- | --- | --- | --- | --- | --- | --- |
|  | FEED | DRAIN | MELT | FEED | DRAIN | MELT | FEED | DRAIN | MELT |
| L-LD (%) | 83 | 55 | 97 | 97 | 89 | 99.2 | 99.2 | 98.5 | 99.5 |
| meso-LD (%) | 8 | 23 | 1.8 | 1.8 | 7 | 0.5 | 0.5 | 1 | 0.3 |
| complex (%) | 1.6 | 6 | 0.3 | 0.3 | 1.5 | 0.1 | 0.1 | 0.2 | 0.1 |
| acidity (meq/kg) | 570 | 1652 | 160 | 160 | 260 | 35 | 35 | — | 10 |
| water (ppm) | 460 | 586 | 230 | 230 | — | 140 | 140 | — | 50 |
| yield (%) | 100 | 28 | 51 | 100 | 13 | 73 | 100 | 5 | 83 |

The L-LD, meso-LD, and complex contents are determined by GC following esterification of the carboxyl compounds. The acidities are titrated with sodium methoxide in an anhydrous solvent, using phenolphthalein as indicator. The water contents were determined by Karl Fisher.

Example 2

A sample of crude lactide containing 77.2% of L-LD, 8.6% of meso-LD, and 1.2% of complex and having a residual acidity of 1 840 meq/kg will undergo a prepurification procedure before purification by recrystallization in a melt medium as in example 1.

25% by weight of cold water are added to 2 583 kg of crude product at 90° C. The mixture is rapidly brought to its crystallization temperature and will remain there for 30 minutes in order to promote the nucleation of the crystals. The temperature is then gradually lowered to 25° C.

The mixture is subsequently drained at 1 500 revolutions/min and 1 553 kg of large white crystals are harvested. The analysis of this product before and after drying features in table II.

TABLE II

|  | Before drying | After drying |
| --- | --- | --- |
| L-LD (%) | 94.3 | 85.8 |
| meso-LD (%) | 0.7 | 0.7 |
| complex (%) | 3.5 | 11.8 |
| water (ppm) | 5000 | 440 |

Since the water content is too high for direct recrystallization in a melt medium, a stream of dry nitrogen is passed through the product at 110° C. for 1.5 h. This treatment reduces the water content to 440 ppm but raises the concentration of complex at the expense of the L-LD.

The dried product obtained from this treatment will undergo two or three stages of purification by recrystallization in a melt medium, in accordance with example 1.

Table III shows an increase in the efficiency of the purification in a melt medium. In effect, with a feed of lower purity, two stages are enough to attain the required quality. The presence of the complex has a strong adverse effect on the mass yield of the fractions harvested during the final purification step.

TABLE III

|  | STAGE 1 | | | STAGE 2 | | |
| --- | --- | --- | --- | --- | --- | --- |
|  | FEED | DRAIN | MELT | FEED | DRAIN | MELT |
| L-LD (%) | 85.8 | 75.8 | 99.1 | 99.1 | 93.3 | 99.5 |
| meso-LD (%) | 0.7 | 1.6 | 0.1 | 0.1 | 1.9 | 0.2 |
| complex (%) | 11.8 | 17.2 | 0.6 | 0.6 | 3.3 | 0.1 |
| acidity | — | — | 68 | 68 | 260 | 9.7 |

TABLE III-continued

|  | STAGE 1 | | | STAGE 2 | | |
| --- | --- | --- | --- | --- | --- | --- |
|  | FEED | DRAIN | MELT | FEED | DRAIN | MELT |
| (meq/kg) | | | | | | |
| water (ppm) | 440 | 670 | 220 | 220 | — | 58 |
| yield (%) | 100 | 44 | 37 | 100 | 9 | 72 |

Example 3

An example of crude lactide containing 84.9% of L-LD, 5.5% of meso-LD, and 3.3% of complex and having a residual acidity of 830 meq/kg will undergo a treatment in accordance with example 2, apart from the draining and drying phases, which are adapted in order to minimize the formation of the complex.

25% by weight of cold water are added to 2 587 kg of crude product at 90° C. The mixture is brought rapidly to its crystallization temperature, where it will remain for 30 min. Thereafter, the temperature is lowered to 25° C.

The mixture is subsequently drained at 2 000 revolutions/min, and 1 786 kg of large white crystals are harvested. These crystals are dried under vacuum at 45° C. in order to extract the free water but also the water which is bound in complex form. In effect, the disappearance of the complex corresponds to an increase in the L-LD content. The analysis of the dried product features in table IV.

TABLE IV

|  | Before drying | After drying |
|---|---|---|
| L-LD (%) | 90.8 | 97.6 |
| meso-LD (%) | 0.9 | 0.7 |
| complex (%) | 5 | 1.1 |
| water (ppm) | 3450 | 370 |

The dried product obtained from this treatment will undergo recrystallizations in a melt medium in accordance with example 1.

Table V shows, by comparison with example 2, an increase in the mass yield of the fractions harvested in this purification process when the amount of complex in the starting product is lower.

TABLE V

|  | STAGE 1 | | | STAGE 2 | | |
|---|---|---|---|---|---|---|
|  | FEED | DRAIN | MELT | FEED | DRAIN | MELT |
| L-LD (%) | 97.6 | 94.1 | 99.2 | 99.2 | 98.7 | 99.6 |
| meso-LD (%) | 0.7 | 1.7 | 0.3 | 0.3 | 0.9 | 0.1 |
| complex (%) | 1.1 | 3.3 | 0.3 | 0.3 | 0.4 | 0.1 |
| acidity (meq/kg) | 230 | 491 | 35 | 35 | 190 | 5.6 |
| water (ppm) | 370 | — | 125 | 125 | — | 37 |
| yield (%) | 100 | 10 | 73 | 100 | 5 | 86 |

Example 4

This example shows the efficiency of the purification for low-lactide mixtures, which are byproducts of the purification process. A sample of crude lactide containing 41.9% of L-LD, 14.3% of meso-LD, and 2.2% of complex will undergo a treatment in accordance with example 3.

25% by weight of cold water are added to 1.082 kg of crude product at 80° C. The mixture is rapidly brought to its crystallization temperature, where it will remain for 30 min. Thereafter, the temperature is lowered to 25° C.

The mixture is subsequently drained and 0.400 kg of large white crystals are harvested and dried. The analysis of the dried product features in table VI.

TABLE VI

|  | Before drying | After drying |
|---|---|---|
| L-LD (%) | 91.1 | 93.2 |
| meso-LD (%) | 2.6 | 2.2 |
| complex (%) | 2.4 | 0.8 |
| water (ppm) | 4200 | 800 |

The dried product obtained from this treatment can be treated by recrystallization in a melt medium in accordance with example 1. Relative to the conventional processes for producing PLA with various recycling regimes, our technique offers the advantage of recycling the lactide as it is and no longer in lactate form.

What is claimed is:

1. A process for purifying the dimeric cyclic ester of lactic acid starting from a crude lactide comprising impurities, the process comprising the following steps:

a) controlled, extractive crystallization of the crude lactide in an aqueous medium, controlling the geometry of the crystals formed and bringing about phase segregation between the lactide and the impurities, promoting aqueous extraction of the impurities;

b) separation of the crystal suspension obtained in (a) into a low-lactide liquid phase loaded with impurities and a lactide-crystal-rich wet cake;

c) drying of the wet cake obtained in (b);

d) recrystallization in a melt medium of the dried impure lactide obtained in (c), and recovery of the purified lactide.

2. The process of claim 1, wherein the crude lactide comprises a mixture of lactic acid and/or lactic ester and their respective oligomers, water and/or alcohol, and the various diastereoisomeric forms of the lactide or mixtures thereof.

3. The process of claim 2, wherein the crude lactide is obtained by mixing fractions originating from lactide purification or synthesis processes.

4. The process of claim 1, wherein the crude lactide has a content of one diastereoisomer of the lactide of between 30 and 90%, a water content of between 0 and 2%, a content of lactic acid and oligomers of lactic acid of between 0 and 50%, and a content of meso-lactide and the other diastereoisomer of the lactide of between 0 and 30%.

5. The process of claim 1, wherein the controlled, extractive crystallization (a) comprises a first phase of progressive seeding of the lactide and a second phase of crystal growth with expulsion of the impurities into the aqueous phase.

6. The process of claim 5, wherein the progressive seeding phase is initiated by maintaining the mixture at a temperature which is slightly lower than the crystallization temperature of the lactide in the mixture.

7. The process of claim 5, wherein the growth phase with extraction of the impurities is assured by a controlled reduction in the temperature of the mixture, promoting the growth of lactide crystals.

8. The process of claim 1, wherein the controlled, extractive crystallization (a) is carried out at a temperature of between 100° C. and 0° C.

9. The process of claim 1, wherein the controlled, extractive crystallization step (a) is carried out on a mixture in which the amount of added water relative to the crude lactide is between 0 and 40%.

10. The process of claim 1, wherein the controlled, extractive crystallization step (a) comprises the use of a reactor with stirring, having a thermostating capacity, and an extraction system which is also suitable for pastelike products, with a residence time of between 1 and 90 min.

11. A composition of the crystal suspension obtained after step (a) of claim 1, comprising in particular a water content of between 1 and 40%, a content of one diastereoisomer of the lactide of between 35 and 90%, a content of lactic acid and oligomers of lactic acid of between 0 and 10%, and a content of meso-lactide and the other diastereoisomer of the lactide.

12. The composition of claim 11, wherein the diastereoisomer of the lactide comprises the lactide per se and a lactide complex which consists of one molecule of lactide bound reversibly by hydrogen bonding to one molecule of water.

13. The process of claim 1, wherein the separation step (b) is a centrifugation separation or other separation which makes it possible to obtain a residual free water content in the wet cake of between 0 and 3%.

14. The process of claim 13, wherein the drying step (c) is replaced by centrifugal solvent washing of the lactide-crystal-rich wet cake obtained in step (b) in order to extract the water from it.

15. The composition of the wet cake obtained after step (b) of claim 1, comprising in particular a free water content of between 0 and 5%, a total lactide content of between 75 and 98%, a content of lactic acid and oligomers of lactic acid of between 0 and 5%, and a content of meso-lactide and the other diastereoisomer of the lactide.

16. The process of claim 1, wherein step (c) comprises a drying procedure which attains a residual free water content in the dried impure lactide of between 0 and 800 ppm, and a residual content of water bound in the form of lactide complex of between 0 and 3%.

17. The process of claim 1, wherein the drying (c) in solid phase of the wet cake obtained from (b) is carried out under vacuum or under a dry gas stream at a temperature of less than 50° C.

18. The process of claim 1, wherein the step of drying (c) in liquid phase comprises the prior liquefaction of the wet cake obtained from (b) and then entrainment of the water, free and bound, by sparging and/or purging of a dry gas stream into the solution.

19. The process of claim 18, wherein the temperature of drying (c), which is slightly greater than the temperature of liquefaction of the wet lactide, is between 90° C. and 130° C.

20. The process of claim 17, wherein the dry gas stream is an inert gas or air and in that this gas stream is preheated where appropriate.

21. The process of claim 1, wherein step (d) comprises one or more recrystallizations in a melt medium of the dried impure lactide obtained in (c).

22. The process of claim 21, wherein a viscosity reducer is mixed with the dried impure lactide obtained from step (c) in order to increase the rate of crystallization, the mass transfer coefficient, and the efficiency of the recrystallization in a melt medium.

23. The process of claim 22, wherein the viscosity reducer is a solvent which is introduced at the end of the drying step (c) and is selected from ketones, ethers, aromatic or aliphatic solvents, silicone-based solvents, halogenated solvents, alcohols, and esters of lactic acid.

24. The process of claim 22, wherein the viscosity reducer is the residual solvent introduced during the step of centrifugal separation (b) of the process and is selected from ketones, ethers, aromatic or aliphatic solvents, silicone-based solvents, halogenated solvents, alcohols, and esters of lactic acid.

25. The process of claim 22, wherein the viscosity reducer content is between 0 and 30%.

26. The process of claim 1, wherein the lactide content at the end of step (d) is between 99.0 and 99.9%, the meso-lactide content is between 0 and 0.5%, the water content, is between 0 and 100 ppm, the amount of lactic acid and oligomers is between 0 and 10 meg/kg.

27. A process for purifying the dimeric cyclic ester of glycolic acid starting from a crude glycolide comprising impurities, the process comprising the following steps:
  a) controlled, extractive crystallization of the crude glycolide in an aqueous medium, controlling the geometry of the crystals formed and bringing about phase segregation between the glycolide and the impurities, promoting aqueous extraction of the impurities;
  b) separation of the crystal suspension obtained in (a) into a low-glycolide liquid phase loaded with impurities and a glycolide-crystal-rich wet cake;
  c) drying of the wet cake obtained in (b);
  d) recrystallization in a melt medium of the dried impure glycolide obtained in (c), and recovery of the purified glycolide.

28. The process of claim 1, wherein the composition of the crystal suspension obtained after step (a) comprises a water content of between about 1 and 40%, a content of one diastereoisomer of the lactide of between about 35 and 90%, a content of lactic acid and oligomers of lactic acid of between about 0 and 10%, and a content of meso-lactide and the other diastereoisomer of the lactide.

29. The process of claim 28, wherein the diastereoisomer of the lactide comprises the lactide per se and a lactide complex which consists of one molecule of lactide bound reversibly by hydrogen bonding to one molecule of water.

30. The process of claim 1, wherein the composition of the wet cake obtained after step (b) comprises a free water content of between 0 and 5%, a total lactide content of between 75 and 98%, a content of lactic acid and oligomers of lactic acid of between 0 and 5%, and a content of meso-lactide and the other diastereoisomer of the lactide.

31. The process of claim 1, wherein the controlled, extractive crystallization step (a) comprises the use of a reactor with stirring, having a thermostating capacity, and an extraction system which is also suitable for pastelike products, with a residence time of between 1 and 60 mm.

* * * * *

UNITED STATES PATENT AND TRADEMARK OFFICE
CERTIFICATE OF CORRECTION

PATENT NO. : 6,800,767 B2
DATED : October 5, 2004
INVENTOR(S) : Van Gansberghe et al.

It is certified that error appears in the above-identified patent and that said Letters Patent is hereby corrected as shown below:

<u>Column 14,</u>
Line 7, after "10" replace "meg/kg" with -- meq/kg --.
Line 44, after "60" replace "mm" with -- min --.

Signed and Sealed this

First Day of February, 2005

JON W. DUDAS
*Director of the United States Patent and Trademark Office*